United States Patent
Owen et al.

(10) Patent No.: US 6,692,797 B1
(45) Date of Patent: Feb. 17, 2004

(54) PHOTOACTIVE PENTAERYTHRITOL DERIVATIVES AND ORIENTATION LAYERS

(75) Inventors: Gareth J Owen, Grimsby (GB); Peregrin O Jackson, Hull (GB); Mary O'Neil, Hull (GB); Stephen M Kelly, Hull (GB)

(73) Assignee: Qinetiq Limited, Hants (GB)

( * ) Notice: Subject to any disclaimer, the term of this patent is extended or adjusted under 35 U.S.C. 154(b) by 0 days.

(21) Appl. No.: 09/936,219
(22) PCT Filed: Mar. 7, 2000
(86) PCT No.: PCT/GB00/00825
§ 371 (c)(1),
(2), (4) Date: Nov. 21, 2001
(87) PCT Pub. No.: WO00/55151
PCT Pub. Date: Sep. 21, 2000

(30) Foreign Application Priority Data

Mar. 12, 1999 (GB) .............................. 9905579

(51) Int. Cl.$^7$ .................. C09K 19/56; G02F 1/1337
(52) U.S. Cl. .................. 428/1.2; 349/124; 524/380; 528/424
(58) Field of Search .................. 428/1.2; 349/123, 349/124; 524/380; 528/424; 558/268

(56) References Cited

U.S. PATENT DOCUMENTS 3,542,841 A * 11/1970 Moore et al. .............. 558/268
6,005,038 A * 12/1999 Yu et al. .................. 524/380

FOREIGN PATENT DOCUMENTS

EP      0 611 786      8/1994
WO      WO 96/10049    4/1996

OTHER PUBLICATIONS

Kremers et al., Synthesis and Characterization of a Chiral Dendrimer Derived from Pentaerythritol, J. Org. Chem., 1994, vol. 59 pp 4262–4266.*
2003 NEC LCD Technologies, 2003.*
Danusso et al, "Structure and solid state photopolymerization of pentaerythrito tetracinnamate", Polymer 18(2):161–163 (1977).
Van De Witte et al, "Optical components from a new vitrifying liquid crystal", Liq. Cryst. 26(7):1039–1046 (1999) XP–000911037.

* cited by examiner

Primary Examiner—Harold Pyon
Assistant Examiner—Sow-Fun Hon
(74) Attorney, Agent, or Firm—Nixon & Vanderhye P.C.

(57) ABSTRACT

Alignment layers for use in liquid crystal devices comprising photoactive pentaerythritol derivatives. 1,2,3,4-trakiskis (8-[2-oxo-2H-1-benzopyran-7-yloxy]octanoyloxy) pentaerythritol is but one example.

12 Claims, 2 Drawing Sheets

PHOTOACTIVE PENTAERYTHRITOL DERIVATIVES AND ORIENTATION LAYERS

This application is a 371 of PCT/GB00/0825 filed Mar. 7, 2000 and claims priority to United Kingdom 99005579, filed Mar. 12, 1999.

BACKGROUND OF THE INVENTION

The present invention describes materials and methods for achieving alignment of liquid crystal materials on a substrate surface and devices fabricated using these methods and materials.

Liquid crystal display devices (LCDs) or light shutters generally comprise a layer of liquid crystalline material between two solid substrates to form a cell. These substrates are generally coated with a conducting material, such as Indium/Tin Oxide (ITO) to form electrodes or electrode patterns. An electric field applied across the cell or between the electrodes switches the liquid crystal between different molecular arrangements or states. Thus the light transmission through the cell can be modulated depending on the cell configuration, the type of liquid crystalline material, the presence of polarisers, etc. A preferred molecular alignment direction and pretilt angle ($\theta$) is imparted by an alignment layer on top of the electrodes and in contact with the liquid crystalline material.

It is well known in the art that fabrication of liquid crystal devices which have advantageous performance and low defect densities requires control of the alignment of the liquid crystalline material at the surfaces of the device. Different types of liquid crystal alignment have been described. Homeotropic alignment refers to an alignment in which the unique optical axis of a liquid crystal phase is held perpendicular to the adjacent surface.

Planar alignment, sometimes referred to as homogeneous alignment, refers to alignment in which the unique optic axis of the liquid crystal phase lies parallel to the adjacent surface. Planar alignment may also impose a direction in which the optic axis of the liquid crystal lies in the plane of the adjacent surface.

Tilted planar alignment or tilted homogeneous alignment refer to alignment in which the liquid crystal unique optic axis lies at an angle, termed the pretilt angle ($\theta$) from the plane of the adjacent surface. The pretilt angle may be as small as a fraction of one degree or as large as several tens of degrees.

Tilted homeotropic alignment refers to an alignment in which the optic axis of the liquid crystal lies tilted away from the normal to the adjacent surface. This deviation is again termed a pretilt angle.

In liquid crystal devices, said alignment geometries are chosen and used in combination to achieve specific optical and electro-optic properties from the device and may be combined in new ways or with new liquid crystalline mixtures to provide new types of devices.

Several methods are known in the art by which defined liquid crystal alignment may be achieved. Deposition of a polymer layer, for example a polyimide layer, on the substrate surface followed by mechanical rubbing provides a pretilted planar alignment. A planar alignment or tilted planar alignment may also be achieved by evaporating a variety of inorganic substances, for example $SiO_x$, onto the surface from an oblique angle of incidence. A disadvantage of this method is that it requires slow and costly vacuum processing. A further disadvantage is that the resulting evaporated layer may show a high capacity to absorb contaminants onto itself from the environment or from other materials used in fabrication of the device.

A homeotropic alignment can be obtained by depositing a surfactant, for example a quaternary ammonium salt, onto the surface from solution in a suitable solvent. A disadvantage of this treatment is that the resistivity of the liquid crystal device may be lowered by the surfactant and the resulting alignment may also show poor stability.

Structured alignment patterns of subpixel size and above can be achieved by illumination of a polymer layer containing photochemically orientable dyes or photochemically dimerisable and/or isomerisable molecules, as described, for example, in EP-A-0445629. A disadvantage of this method is that the solubility of the dye molecules in the polymer matrix is limited and the chemical and photochemical stability over time is insufficient.

Another method for achieving structured non-contact orientation is the photodimerisation of polymers incorporating photodimerisable groups, such as cinnamate or coumarin derivatives, as described, for example, in Jpn. J. Appl. Phys., Vol., 31, 2155 (1995) and EP-A-9410699.0. A disadvantage of these materials is the polydispersity of the materials produced by polymerisation. This requires, for example, different solution concentrations for spin coating depending on the average molecular weights of the polymers which can not be determined with any great accuracy and which are often not reproducible from one batch to another. This can give rise to unreproducible alignment as well as also requiring repeated purification cycles of the polymer product in order to remove unreacted monomer and oligomers. The attachment of low molar mass photoreactive units to monodispersed polymer backbones can lead to polymers with unreacted sites, which can give rise to dielectric breakdown of cells containing such materials. This is especially important for active matrix devices.

An object of this invention is to provide means of achieving a defined surface alignment of a liquid crystalline material on a substrate surface, which does not require mechanical rubbing or other methods of physical contact which may damage the surface or structures on the surface. This is especially important for active matrix displays based on the use of surface mounted thin film transistors. Static electricity or dust caused by mechanical rubbing or buffing polymer layers, such as polyimide or polyamide, in order to induce a unidirectional alignment due to microgrooves can cause defects in thin film transistors and lead to dielectric breakdown. Such alignment layers also suffer from the disadvantage that the microgrooves possess inherent defects themselves, which can result in random phase distortion and light scattering. This impacts detrimentally on the optical appearance of the displays or the efficiency of the light shutters. Additionally, mechanical buffing does not allow locally oriented regions of the surface to be aligned with different azimuthal angles. This is a substantial drawback since sub-pixelisation can lead to higher contrast and an improved optical efficiency.

SUMMARY OF THE INVENTION

According to this invention materials are provided of Formula I:

Formula I where

$X_{1-8}$ are each independently selected from: H, halogen, CN, OH, straight or branched chain alkyl having from 1 to 16 carbon atoms, where one or more non-adjacent $CH_2$ groups may be substituted by $CH(CN)$, $CH(CF_3)$, CHF, CHCl, $CH(CH_3)$;

$S_{1-8}$ are spacer units;

$PG_{1-4}$ are photopolymerisable/dimerisable groups $m_1$, $m_2$, $m_3$, and $m_4$ are each independently selected from the integers 1 and 0;

$A_{1-8}$ are each independently selected from the aromatic rings:

where ~ indicates a sigma bond between part of the molecule shown in formula I and a carbon atom at any position in one of the aromatic rings;

and where the CH groups present in the aromatic rings may each be independently substituted by C(CN), $C(CF_3)$, C-halogen, $C(CH_3)$, CR, where R is selected from straight or branched chain alkyl and may include from 1 to 8 carbon atoms and including where one or more non-adjacent $CH_2$ groups may be substituted by CH(CN), $CH(CF_3)$, CHF, CHCl, $CH(CH_3)$.

Preferably the spacer groups $S_{1-4}$ are, independently of one another, selected from groups having the general formula:

$$L_1-(CH_2)_n-L_2$$

where: n=1 to 30, where each $CH_2$ group present in the chain linking $L_1$ and $L_2$ may be independently substituted by CH(CN), $CH(CF_3)$, CHF, CHCl, $CH(CH_3)$, $L_1$ and $L_2$ are independently selected from: single covalent bond, O, COO, OOC, $CH_2O$, and $OCH_2$. More preferably $S_{1-4}$ are independently selected from oxycarbonylalkanoyloxy, oxyalkoxy, oxycarbonylalkoxy, oxyalkanoyloxy, oxycarbonylphenoxyalkanoyloxy, oxyalkoxyalkyl containing from 1–16 carbon atoms.

In a preferred embodiment spacer groups $S_{5-8}$ are each independently selected from: COO, OOC, C≡C, C=C, single covalent bond.

Preferably the photopolymerisable/dimerisable groups $PG_{1-4}$ are each independently selected from:

where a sigma bond exists between part of the molecule shown in formula I and any one of the four C atoms that are in the benzene ring to which G is fused and that do not form part of the ring G; and where CH groups present in the benzene ring to which the ring G is fused may each be independently substituted by C(CN), $C(CF_3)$, C-halogen, $C(CH_3)$, CR, where R is selected from straight or branched chain alkyl and may include from 1 to 8 carbon atoms and including where one or more non-adjacent $CH_2$ groups may be substituted by CH(CN), $CH(CF_3)$, CHF, CHCl, $CH(CH_3)$;

where G is independently selected from:

and where J is independently selected from:

$R_1$ may be H, halogen, CN, $NO_2$, NCS, SCN, alkyl with 1 to 12 carbon atoms which is optionally substituted with one or more fluorines and in which optionally 1 or 2 non-adjacent methylene units ($CH_2$) can be replaced by oxygen, COO, OOC, CO and/or CH=CH;

$R_2$ may be H or $C_{1-10}$ alkyl;

$D_1$ may be H, alkyl or alkoxy with 1 to 8 carbon atoms, trifluoromethyl, or phenyl which may be substituted from one and up to and including all available substitution positions with one or more of the groups selected from CN, halogen, $NO_2$;

$E_1$ may be H, alkyl or alkoxy with 1 to 8 carbon atoms, cyano, or $COOR_5$;

$R_5$ may be $C_{1-10}$ alkyl.

$D_2$ may be H, alkyl or alkoxy with 1 to 8 carbon atoms, trifluoromethyl, or phenyl which may be substituted from one and up to and including all available substitution positions with one or more of the groups selected from CN, halogen, $NO_2$;

$E_2$ may be H, alkyl or alkoxy with 1 to 8 carbon atoms, cyano, or $COOR_6$;

$R_6$ may be $C_{1-10}$ alkyl.

$D_3$ may be H, alkyl or alkoxy with 1 to 8 carbon atoms, trifluoromethyl, or phenyl which may be substituted from one and up to and including all available substitution positions with one or more of the groups selected from CN, halogen, $NO_2$;

$E_3$ may be H, alkyl or alkoxy with 1 to 8 carbon atoms, cyano, or $COOR_7$;

$R_7$ may be $C_{1-10}$ alkyl.

$D_4$ may be H, alkyl or alkoxy with 1 to 8 carbon atoms, trifluoromethyl, or phenyl which may be substituted from one and up to and including all available substitution positions with one or more of the groups selected from CN, halogen, $NO_2$;

$E_4$ may be H, alkyl or alkoxy with 1 to 8 carbon atoms, cyano, or $COOR_8$;

$R_8$ may be $C_{1-10}$ alkyl.

$D_5$ may be H, alkyl or alkoxy with 1 to 8 carbon atoms, trifluoromethyl, or phenyl which may be substituted from one and up to and including all available substitution positions with one or more of the groups selected from CN, halogen, $NO_2$;

$E_5$ may be H, alkyl or alkoxy with 1 to 8 carbon atoms, cyano, or $COOR_9$;

$R_9$ may be $C_{1-10}$ alkyl.

$D_6$ may be H, alkyl or alkoxy with 1 to 8 carbon atoms, trifluoromethyl, or phenyl which may be substituted from one and up to and including all available substitution positions with one or more of the groups selected from CN, halogen, $NO_2$;

$E_5$ may be H, alkyl or alkoxy with 1 to 8 carbon atoms, cyano, or $COOR_9$;

$R_9$ may be $C_{1-10}$ alkyl.

Examples of the term "alkyl with 1 to 12 carbon atoms which is optionally substituted with one or more fluorines and in which optionally 1 or 2 non-adjacent methylene units ($CH_2$) can be replaced by oxygen, COO, OOC, CO and/or CH=CH" include in the present application straight-chain and branched (optionally chiral) residues such as alkyl, alkenyl, alkoxy, alkenyloxy, alkoxyalkyl, alkoxyalkenyl, 1-fluoroalkyl, terminal trifluoromethylalkyl, terminal difluoromethylalkyl, terminal trifluoromethylalkoxy, and the like with 1 or, 2 to 16 carbon atoms. Examples of preferred residues are methyl, ethyl, propyl, butyl, pentyl, hexyl, heptyl, octyl, 1-methylpropyl, 1-methylheptyl, 2-methylbutyl, 3-methyl pentyl, vinyl, 1E-propenyl, 1E-butenyl, 1E-pentenyl, 3-butenyl, 3E-pentenyl, 3E-hexenyl, 3E-hexenyl, 4-pentenyl, 4Z-hexenyl, 5-hexenyl, 6-heptenyl, 7-octenyl, methoxy, ethoxy, propyloxy, butyloxy, pentyloxy, hexyloxy, octyloxy, 1-methylpropyloxy, 1-methylheptyloxy, 2-methylbutyloxy, 1-fluoropropyl, 2-fluoropropyl, 2,2-difluoropropyl, 3-fluoropropyl, 3,3-difluoropropyl, 3,3,3-trifluoropropyl and the like. Especially preferred residues possess 1 or, respectively, 2 to 6 carbon atoms.

The term "halogen" may represent in the present application fluorine, chlorine, bromine and iodine, but especially fluorine and chlorine.

According to an aspect of this invention a method is provided for forming an alignment layer on a surface of a liquid crystal cell wall, the method comprising the steps: depositing a layer of a material comprising at least one compound of Formula I on the surface; and exposing the material to actinic radiation.

Preferably the method for forming an alignment layer further comprises the step of controlling the exposure time and/or intensity of the actinic radiation used to provide a selected value of pretilt in a liquid crystal placed in contact with the exposed layer.

Preferably the radiation includes light, with a wavelength of 250–450 nm. More preferably the radiation is light with a wavelength of 300–400 nm.

According to a further aspect of this invention a liquid crystal device comprises a layer of a liquid crystal material contained between two cell walls both carrying electrode structures and surface treated to provide an alignment layer for liquid crystal molecules;

characterised in that:
the alignment layer comprises a compound of Formula 1 that has been exposed to actinic radiation.

Preferably the alignment layer comprises a compound of Formula I that has been exposed to actinic radiation, the exposure time and/or intensity of the actinic radiation used being controlled to provide a selected value of pretilt in a liquid crystal placed in contact with the exposed layer.

Preferably the radiation includes light, with a wavelength of 250–450 nm. More preferably the radiation is light with a wavelength of 300–400 nm.

Compounds of Formula I can be prepared by various routes from commercially available starting materials. Typically tetrakis(hydroxymethyl)methane (pentaerythritol) can be esterified with ω-halogenoalkanoic acids in the presence of N,N-dicyclohexylcarbodiimide and 4-(dimethylamino) pyridine and a polar solvent, such as N,N-dimethylformamide or dichloromethane. The resultant bromides can then be alkylated in a Williams ether synthesis with phenols incorporating a photoisomerisable/dimerisable group, such as coumarin or cinnamate, in the presence of a base, such as potassium carbonate, and a polar solvent, such as cyclohexanone or ethyl-methylketone. The bromides can also be esterified with a photoisomerisable/dimerisable group, such as cinnamic acids, in the presence of DBU and a non polar solvent, such as toluene or benzene. Similarly pentaerythritol can be alkylated with ω-halogenoalkanols protected, for example as the THP derivative, in the presence of base, such as potassium tert.-butylate, and a polar solvent, such as 1,2-dimethoxyethane or ethylene glycol dimethyl ether. After deprotection the resultant alcohols can then be esterified with a photoisomerisable/dimerisable group, such as aromatic acids incorporating a cinnamate or coumarin moiety, in the presence of N,N-dicyclohexylcarbodiimide and 4-(dimethylamino)pyridine and a polar solvent, such as N,N-dimethylformamide or dichloromethane. The alcohols can also be alkylated in a Mitsunobu reaction, with a photoisomerisable/dimerisable group, such as 6-hydroxycoumarin, 7-hydroxycoumarin (umbelliferone) or alkyl hydroxycinnamates, in the presence of a dehydrating agent, such as diethyl azodicarboxylate and triphenyl phosphine, and a polar solvent, such as tetrahydrofuran or N,N-dimethylformamide.

The photocross-linkable groups, such as cinnamic acids, cinnamate esters, cinnamonitriles, styrenes, stilbenes, vinylnaphthalenes, vinylpyridines, maleimides, thymines, coumarins, are generally are either commercially available or readily accessible, for example coumarin and cinnamate derivatives can be prepared according to literature methods, such as the Perkin, Pechmann, Knoevenagel, Wittig-Homer, Heck or sigmatropic rearrangement reactions (Organic Reactions, 1, 210, 1942; Organic Reactions, 15, 204, 1967; Synthesis, 131, 1978; J. Mol. Cat., 88, L113, 1994; J. Chem. Soc. Perkin Trans. I, 1753, 1987).

In order to obtain alignment layers in regions selectively limited by area, a solution of the photoactive pentraerythritol derivative can, for example, firstly be prepared and then spread out using a spin-coating apparatus on a carrier coated with an electrode, e.g., a glass plate coated with indium-tin oxide (ITO) such that homogeneous layers of 0.05–50 $\mu$m thickness result. Subsequently or simultaneously, irradiation can be applied to the region to be isomerised and/or dimerised (cross-linked), e.g., with a mercury high pressure lamp, a xenon lamp or a UV laser utilising a polariser and optionally a mask for the formation of structures. The duration and irradiation depends on the capacity of the individual lamps and can vary from a few minutes to several hours. The cross-linking can, however, also effected by irradiating the homogeneous layer using filters which, e.g., let through only radiation suitable for the cross-linking reaction. Photosensitisors, such as acetophenone or benzophenone may be added to shorten the illumination time required for cross-linking. Non-zero tilt angles ($\theta$) may be induced by illumination with plane polarised light from a non-perpendicular angle to the plane of the substrate.

BRIEF DESCRIPTION OF DRAWINGS

The invention will now be described, by way of example only, with reference to the following examples and diagrams.

DETAILED DESCRIPTION OF INVENTION

Figure 1:
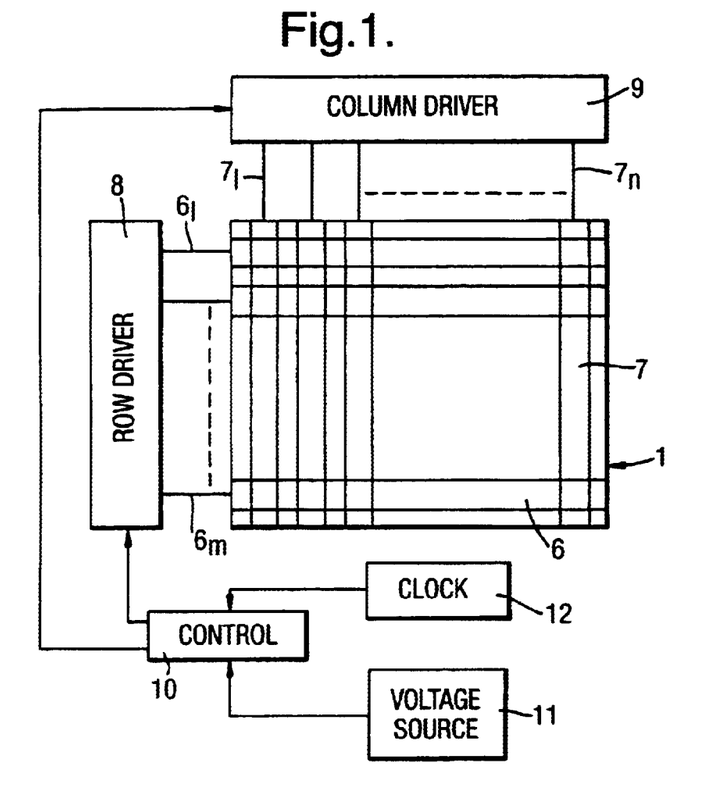
FIG. 1 is a plan view of a matrix multiplex addressed liquid crystal display.
Figure 2:
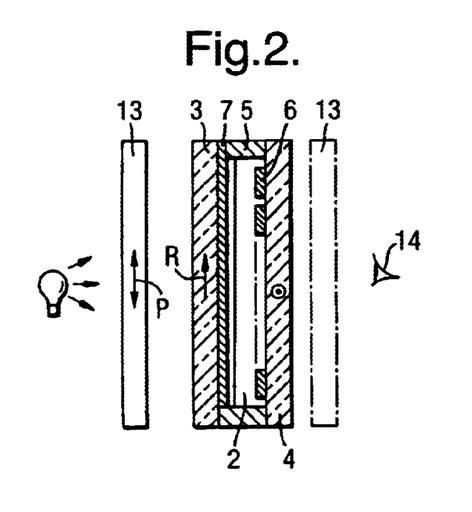
FIG. 2 is a cross-section of a display such as FIG. 1 used in a transmissive mode.
Figure 3:
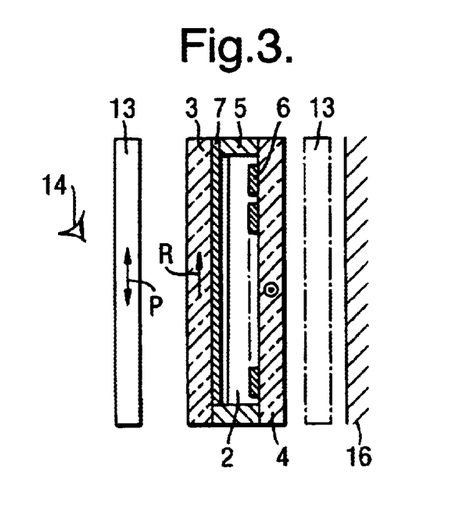
FIG. 3 is similar to FIG. 2 but operates in a reflective mode.

The device of FIGS. 1, 2 and 3 comprises a liquid crystal cell 1 formed by a layer of a liquid crystal material 2 contained between two glass walls 3, 4 spaced typically 1 to 15 $\mu$m apart by a spacer ring 5. The inside faces of both walls 3, 4 are coated with electrodes 6. The electrodes may be of sheet like form covering the complete wall, or formed into for example, strip electrodes to provide an array of addressable electrode intersections. The walls are also coated with an aligning layer (not shown) of material described by the current invention.

If the material 2 is nematic then the device may be the known super twisted nematic device, also known as a STN device. In this case polarisers 13 are used to distinguish between the device voltage ON and OFF states.

The liquid crystal material may be nematic, chiral nematic (cholesteric), or smectic (e.g., ferroelectric) material. The device may be used as a display device, e.g., displaying alpha numeric information, or an x, y matrix displaying information. alternatively the device may operate as a shutter to modulate light transmission, e.g., as a spatial light modulator, or as a privacy window.

For passive matrix devices (shown in FIG. 1) strip like row electrodes $6_1$, to $6_m$, e.g. of InSnO$_2$ are formed on one wall 3 and similar column electrodes $7_1$ to $7_n$ formed on the other wall 4. With m-row electrodes and n-column electrodes this forms an mxn matrix of addressable elements. Each element is formed by the interaction of a row and column electrode. For active matrix devices a discrete nonlinear device eg a transistor or diode is associated with each pixel.

For the passive matrix device a row driver supplies voltage to each row electrode 6. Similarly a column drive 9 supplies voltages to each column electrode 7. Control of applied voltages is from a control logic 10 which receives power from a voltage source 11 and timing from a clock 12.

For an active device e.g., a thin film transistor active matrix liquid crystal device (TFT AMLCD) three types of electrodes are present, pixel, scanning and signal electrodes as well as a common electrode on the opposite side of the liquid crystal. The control electrode operates the gate such that the voltage on the signal electrode is applied to the relevant pixel electrode.

An example of the use of a material and device embodying the present invention will now be described with reference to FIG. 2.

The liquid crystal device consists of two transparent plates, 3 and 4, for example made from glass, in the case of an active matrix device these will usually be ofaluminosilicate (alkali free) glass often with a passivation layer of SiO$_2$. For an active matrix display the active devices eg thin film transistors, are fabricated and the colour filter layer is added for a full colour display. These plates are coated on their internal face with transparent conducting electrodes 6 and 7, often ITO which is patterned using photolithography techniques. The transparent plates 3 and 4 are coated with a photoactive sample, comprising one or more compounds according to the invention. A typical coating procedure involves the dissolution of one of the compounds of the invention in a solvent, for example cyclopentanone, followed by spin coating of the photoactive compound on the transparent plate. Once the photoactive compound has been coated onto the plates it is exposed to actinic radiation to induce cross-linking of the photoactive molecules. The cross-linking process can be monitored by measuring the birefringence of the alignment layer. The intersections between each column and row electrode form an x, y matrix of addressable elements or pixels. A spacer 5 e.g. of polymethyl methacrylate separates the glass plates 3 and 4 to a suitable distance e.g. 2–7 microns preferably 4–6 microns. Liquid crystal material 2 is introduced between glass plates 3,4 by filling the space in between them. This may be done by flow filling the cell using standard techniques. The spacer 5 is sealed with an adhesive in a vacuum using an existing technique. Polarisers 13 may be arranged in front of and behind the cell.

The device may operate in a transmissive or reflective mode. In the former, light passing through the device, e.g. from a tungsten bulb, is selectively transmitted or blocked to form the desired display. In the reflective mode a mirror, or diffuse reflector, (16) is placed behind the second polariser 13 to reflect ambient light back through the cell and two polarisers. By making the mirror partly reflecting the device may be operated both in a transmissive and reflective mode.

The alignment layers have two functions, one to align contacting liquid crystal molecules in a preferred direction and the other to give a tilt to these molecules—a so called surface tilt—of a few degrees typically around 4° or 5°. In an alternative embodiment a single polariser and dye material may be combined. The materials of the current invention may also be used in LCDs with an actively addressed matrix e.g. thin film transistors (TFT-LCDs) or a passively addressed matrix e.g., dual scan STN.

Figure 4:
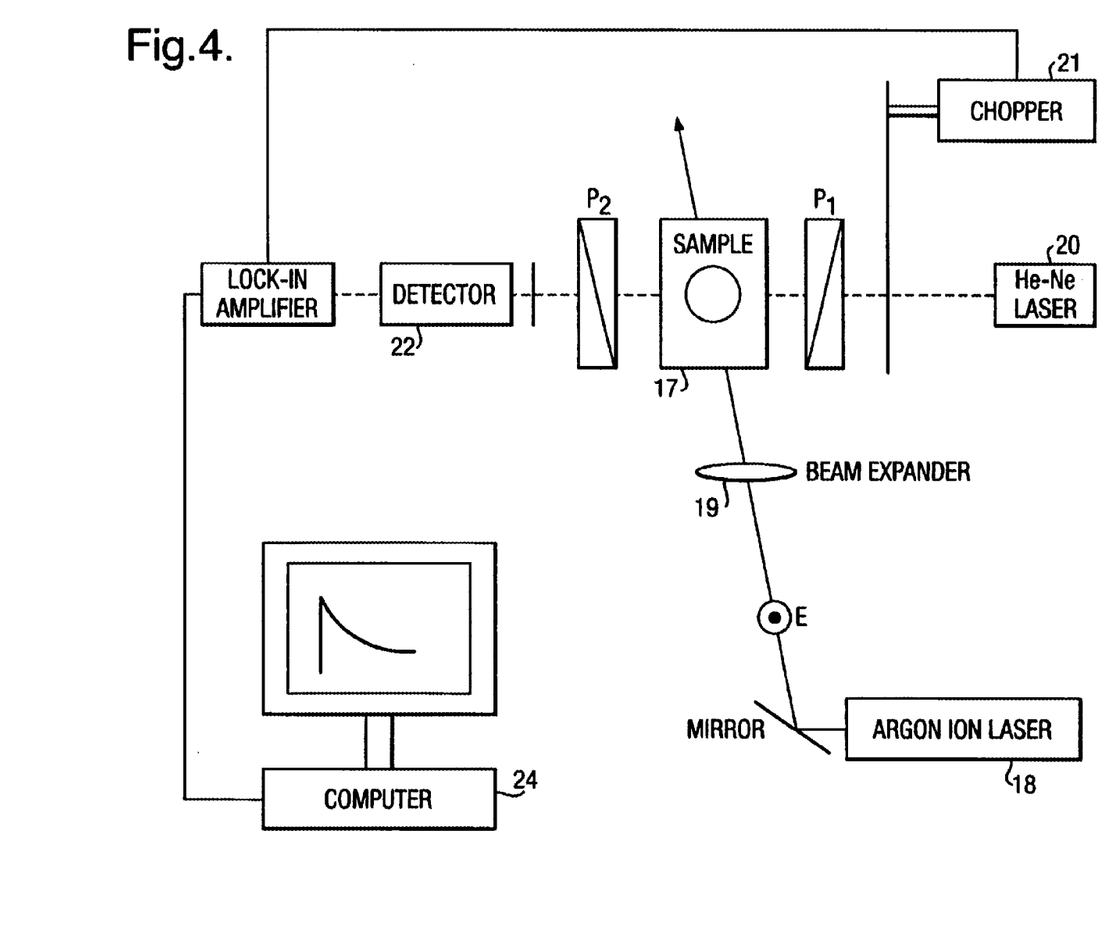
FIG. 4 is a schematic representation of the apparatus used to illuminate the photocross-linkable propane derivatives on a suitable substrate to be used as part of a liquid crystal device.

The apparatus of FIG. 4 used to generate photoinduced anisotropy in a photoactive sample 17, comprising a photoactive pentaerythrol derivative according to the invention, using linearly polarised UV light comprises a radiation source e.g. an argon ion laser 18 (Spectra Physics, Model 2045). The laser beam operating at 300.5 nm has a polarisation direction (E). The laser beam was expanded by using a quartz lens beam expander 19. The film anisotropy is measured by determining the induced birefringence against UV exposure time using a He—Ne laser 20 (632.8 nm) modulated by a rotating chopper 21. The probing wavelength does not perturb the anisotropy inducing process since it is far away from any intrinsic absorption band in either the starting material or photoproduct. During the UV exposure of the sample, the photoinduced birefringence was monitored using two crossed polarisers, P1 and P2 arranged at +/−45° with respect to the vertical polarisation of the UV laser beam. The intensity of the beam from the probing He—Ne laser 20, which then passed through the sample, was detected by a photodetector 22. The birefringence measuring signal taken from the photodetector 22 was processed by a phase sensitive lock-in amplifier 20 and recorded by a computer 24. Data were plotted as birefringence versus UV exposure time. In this way the cross-linking process can be induced and monitored.

The photocross-linkable pentaerythritol derivatives and resultant alignment layers may be produced as described, by way of example only, in the following examples; K signifies the crystalline state, I signifies the isotropic phase, $T_g$ is the glass transition temperature.

EXAMPLE 1

Preparation of 1,2,3,4-Tetrakiskis(8-[2-oxo-2H-1-benzopyran-7-yloxy]octanoyloxy)pentaerythritol A mixture of 3.0 g 1,2,3,4-tetrakis(8-bromooctanoyloxy)pentaerythritol, 2.0 g 7-hydroxycoumarin, 5.0 g anhydrous potassium carbonate and 50 ml ethyl-methyl ketone was heated under gentle reflux overnight. The reaction mixture was filtered to remove inorganic material and the filtrate evaporated down. The residue was purified by column chromatography on silica gel using hexane/ethyl acetate (1/1 v/v) as eluent and recrystallisation from acetonitrile to yield 2.1 g of 1,2,3,4-tetrakis(8-[2-oxo-2H-1-benzopyran-7-yloxy]octanoyloxy)pentaerythritol as an oil.

The 1,2,3,4-tetrakis(8-bromooctanoyloxy)pentaerythritol required as starting material was prepared as follows:

12.0 g Dicyclohexylcarbodiimide was added to a solution of 2.0 g pentaerythritol, 13.0 g 8-bromooctanoic acid, 1.8 g 4-(dimethylamino)pyridine and 50 ml dichloromethane at 0° C. The reaction mixture was stirred overnight at room temperature, filtered to remove inorganic material and the filtrate evaporated down. The residue was purified by column chromatography on silica gel using hexane/ethyl acetate (1/1 v/v) as eluent and recrystallisation from acetonitrile to yield 6.5 g of 1,2,3,4-tetrakis(8-bromooctanoyloxy)pentaerythritol as an oil.

The following compounds can be prepared in an analogous manner:

1,2,3,4-tetrakis(3-[2-oxo-2H-1-benzopyran-7-yloxy]propanoyloxy)pentaerythritol.

1,2,3,4-tetrakis(4-[2-oxo-2H-1-benzopyran-7-yloxy]butanoyloxy)pentaerythritol.

1,2,3,4-tetrakis(5-[2-oxo-2H-1-benzopyran-7-yloxy]pentanoyloxy)pentaerythritol.

1,2,3,4-tetrakis(6-[2-oxo-2H-1-benzopyran-7-yloxy]hexanoyloxy)pentaerythritol.

1,2,3,4-tetrakis(7-[2-oxo-2H-1-benzopyran-7-yloxy]heptanoyloxy)pentaerythritol.

1,2,3,4-tetrakis(9-[2-oxo-2H-1-benzopyran-7-yloxy]nonanoyloxy)pentaerythritol.

1,2,3,4-tetrakis(10-[2-oxo-2H-1-benzopyran-7-yloxy]decanoyloxy)pentaerythritol.

1,2,3,4-tetrakis(3-[2-oxo-2H-1-benzopyran-6-yloxy]propanoyloxy)pentaerythritol.

1,2,3,4-tetrakis(4-[2-oxo-2H-1-benzopyran-6-yloxy]butanoyloxy)pentaerythritol.

1,2,3,4-tetrakis(5-[2-oxo-2H-1-benzopyran-6-yloxy]pentanoyloxy)pentaerythritol.

1,2,3,4-tetrakis(6-[2-oxo-2H-1-benzopyran-6-yloxy]hexanoyloxy)pentaerythritol.

1,2,3,4-tetrakis(7-[2-oxo-2H-1-benzopyran-6-yloxy]heptanoyloxy)pentaerythritol.

1,2,3,4-tetrakis(8-[2-oxo-2H-1-benzopyran-6-yloxy]octanoyloxy)pentaerythritol.

1,2,3,4-tetrakis(9-[2-oxo-2H-1-benzopyran-6-yloxy]nonanoyloxy)pentaerythritol.

1,2,3,4-tetrakis(10-[2-oxo-2H-1-benzopyran-6-yloxy]decanoyloxy)pentaerythritol.

1,2,3,4-tetrakis[3-(4-[(E)-methoxycarbonylethenyl]phenoxy)propanoyloxy]pentaerythritol.

1,2,3,4-tetrakis[3-(4-[(E)-ethoxycarbonylethenyl]phenoxy)propanoyloxy]pentaerythritol.

1,2,3,4-tetrakis[4-(4-[(E)-ethoxycarbonylethenyl]phenoxy)butanoyloxy]pentaerythritol.

1,2,3,4-tetrakis[5-(4-[(E)-ethoxycarbonylethenyl]phenoxy)pentanoyloxy]pentaerythritol.

1,2,3,4-tetrakis[6-(4-[(E)-ethoxycarbonylethenyl]phenoxy)hexanoyloxy]pentaerythritol.

1,2,3,4-tetrakis[7-(4-[(E)-ethoxycarbonylethenyl]phenoxy)heptanoyloxy]pentaerythritol.

1,2,3,4-tetrakis[8-(4-[(E)-ethoxycarbonylethenyl]phenoxy)octanoyloxy]pentaerythritol.

1,2,3,4-tetrakis[8-(4-{2-[(E)-ethoxycarbonylethenyl]thiophen-5-yl}phenoxy)octanoyloxy]pentaerythritol.

1,2,3,4-tetrakis[8-(4-{2-[(E)-ethoxycarbonylethenyl]furan-5-yl}phenoxy)octanoyloxy]pentaerythritol.

1,2,3,4-tetrakis[8-(4-{2-[(E)-ethoxycarbonylethenyl]pridin-5-yl}phenoxy)octanoyloxy]pentaerythritol.

1,2,3,4-tetrakis[8-(4-{2-[(E)-ethoxycarbonylethenyl]primidin-5-yl}phenoxy)octanoyloxy]pentaerythritol.

1,2,3,4-tetrakis[3-(4-[(E)-ethoxycarbonylethenyl]biphenyl-4'-yloxy)propanoyloxy]pentaerythritol.

1,2,3,4-tetrakis[4-(4-[(E)-ethoxycarbonylethenyl]biphenyl-4'-yloxy)butanoyloxy]pentaerythritol.

1,2,3,4-tetrakis[5-(4-[(E)-ethoxycarbonylethenyl]biphenyl-4'-yloxy)pentanoyloxy]pentaerythritol.

1,2,3,4-tetrakis[6-(4-[(E)-ethoxycarbonylethenyl]biphenyl-4'-yloxy)hexanoyloxy]pentaerythritol, Mpt 187° C.

1,2,3,4-tetrakis[7-(4-[(E)-ethoxycarbonylethenyl]biphenyl-4'-yloxy)heptanoyloxy]pentaerythritol.

1,2,3,4-tetrakis[8-(4-[(E)-ethoxycarbonylethenyl]biphenyl-4'-yloxy)octanoyloxy]pentaerythritol.

EXAMPLE 2

Preparation of 1,2,3,4-Tetrakis(4-[(E)-ethoxycarboxyethenyl]biphenyl-4'-yloxy) pentaerythritol 2.6 g Diethyl azodicarboxylate was added to a solution of 3.7 g 4-[(E)-ethoxycarboxyethenyl]4'-hydroxybiphenyl, 0.57 g pentaerythritol, 3.9 g triphenyl phosphine and 50 ml tetrahydrofuran at 0° C. The reaction mixture was stirred overnight at room temperature and then evaporated down with silica gel. The resultant powder was purified by column chromatography on silica gel using hexane/ethyl acetate (1/1 v/v) as eluent and recrystallisation from ethanol to yield 2.1 g of 1,2,3,4-tetrakis(4-[(E)-ethoxycarboxyethenyl]biphenyl-4'-yloxy)pentaerythritol; Mpt 241° C.

The 4-[(E)-ethoxycarboxyethenyl]-4'-hydroxybiphenyl required as starting material is prepared as follows:

A mixture of 10.0 g 4-bromo-4'-hydroxybiphenyl, 6.9 g methyl acrylate, 8.1 g triethylamine, 0.1 g palladium(II) acetate, 0.4 g tri(o-toluyl)phosphine and 30 ml acetonitrile was heated under gentle reflux overnight. The reaction mixture was diluted with 200 ml acetonitrile, filtered to remove inorganic material and the filtrate evaporated down. The residue was purified by precipitation from a dichloromethane solution into hexane and recrystallisation from acetonitrile to yield 7.2 g of 4-[(E)-ethoxycarboxyethenyl]-4'-hydroxybiphenyl; Mpt 228° C.

The following compounds can be prepared in an analogous manner 1,2,3,4-tetrakis(2-oxo-2H-1-benzopyran-7-yloxy) pentaerythritol. carbonyl)phenoxy]dodecanoyloxy) propane.

1,2,3,4-tetrakis(2-oxo-2H-1-benzopyran-6-yloxy) pentaerythritol. carbonyl)phenoxy]dodecanoyloxy) propane.

1,2,3,4-tetrakis(4-[(E)-methoxycarboxyethenyl]phenoxy) pentaerythritol.

1,2,3,4-tetrakis(4-[(E)-ethoxycarboxyethenyl]phenoxy) pentaerythritol.

1,2,3,4-tetrakis(4-[(E)-methoxycarboxyethenyl]biphenyl-4'-yloxy)pentaerythritol.

1,2,3,4-tetrakis(4-[(E)-methoxycarboxyethenyl]-p-terphenyl-4''-yloxy)pentaerythritol.

EXAMPLE 3

Preparation of 1,2,3,4-Tetrakiskis(6-[4-{2-oxo-2H-1-benzopyran-7-yloxycarbonyl}phenoxy] hexanoyloxy)pentaerythritol A mixture of 0.7 g 1,2,3,4-tetrakis(5-bromohexanoyloxy) pentaerythritol, 1.0 g 2-oxo-2H-1-benzopyran-7-yl 4-hydroxybenzoate, 5.0 g anhydrous potassium carbonate and 50 ml ethyl-methyl ketone is heated under gentle reflux overnight. The reaction mixture is filtered to remove inorganic material and the filtrate evaporated down. The residue is purified by column chromatography on silica gel using hexane/ethyl acetate (1/1 v/v) as eluent and recrystallisation from acetonitrile to yield 1.2 g of 1,2,3,4-tetrakiskis(6-[4-{2-oxo-2H-1-benzopyran-7-yloxycarbonyl}phenoxy] hexanoyloxy)pentaerythritol.

The 2-oxo-2H-1-benzopyran-7-yl 4-hydroxybenzoate required as starting material was prepared as follows:

13.4 g triphenylphosphine is added to a solution of 8.3 g 7-hydroxycoumarin, 10.0 g 4-methoxycarbonyloxybenzoic acid, 8.9 g diethyl azodicarboxylate and 50 ml tetrahydrofuran at 0° C. The reaction mixture was stirred overnight at room temperature, filtered to remove inorganic material and the filtrate evaporated down, taken up in warm hexane, filtered to remove inorganic material and evaporated down again. The residue is purified by column chromatography on silica gel using hexane/ethyl acetate (1/1 v/v) as eluent and recrystallisation from acetonitrile to yield 12.2 g of 2-oxo-2H-1-benzopyran-7-yl 4-methoxycarbonyloxybenzoate.

50 ml of saturated ethanolic ammonia solution is added dropwise to a solution of 12.2 g of 2-oxo-2H-1-benzopyran-7-yl 4-methoxycarbonyloxybenzoate in 200 ml of ethanol. The reaction mixture is stirred for two hours, evaporated down and taken up in 100 ml diethyl ether. This solution is washed with water, dried, filtered to remove inorganic material and the filtrate evaporated down. The residue is purified by column chromatography on silica gel using hexane/ethyl acetate (1/1 v/v) as eluent and recrystallisation from acetonitrile to yield 9.5 g of 2-oxo-2H-1-benzopyran-7-yl 4-hydroxybenzoate.

The following compounds can be prepared in an analogous manner:

1,2,3,4-tetrakiskis(3-[4-{2-oxo-2H-1-benzopyran-7-yloxycarbonyl}phenoxy]propanoyloxy) pentaerythritol.

1,2,3,4-tetrakiskis(4-[4-{2-oxo-2H-1-benzopyran-7-yloxycarbonyl}phenoxy]butanoyloxy)pentaerythritol.

1,2,3,4-tetrakiskis(5-[4-{2-oxo-2H-1-benzopyran-7-yloxycarbonyl}phenoxy]pentanoyloxy)pentaerythritol.

1,2,3,4-tetrakiskis(7-[4-{2-oxo-2H-1-benzopyran-7-yloxycarbonyl}phenoxy]heptanoyloxy)pentaerythritol 1,2,3,4-tetrakiskis(8-[4-{2-oxo-2H-1-benzopyran-7-yloxycarbonyl}phenoxy]octanoyloxy)pentaerythritol 1,2,3,4-tetrakiskis(3-[4-{2-oxo-2H-1-benzopyran-6-yloxycarbonyl}phenoxy]propanoyloxy) pentaerythritol.

1,2,3,4-tetrakiskis(4-[4-{2-oxo-2H-1-benzopyran-6-yloxycarbonyl}phenoxy]butanoyloxy)pentaerythritol.

1,2,3,4-tetrakiskis(5-[4-{2-oxo-2H-1-benzopyran-6-yloxycarbonyl}phenoxy]pentanoyloxy)pentaerythritol.

1,2,3,4-tetrakiskis(6-[4-{2-oxo-2H-1-benzopyran-6-yloxycarbonyl}phenoxy]hexanoyloxy)pentaerythritol.

1,2,3,4-tetrakiskis(7-[4-{2-oxo-2H-1-benzopyran-6-yloxycarbonyl}phenoxy]heptanoyloxy)pentaerythritol 1,2,3,4-tetrakiskis(8-[4-{2-oxo-2H-1-benzopyran-6-yloxycarbonyl}phenoxy]octanoyloxy)pentaerythritol

EXAMPLE 4

Preparation of Aligned Twisted and Planar Nematic Cells

A 2 w/w % solution of 1,2,3,4-tetrakis(8-[2-oxo-2H-1-benzopyran-7-yloxy]octanoyloxy)pentaerythritol in cyclopentanone was spin coated at 3000 rpm for 30 seconds onto indium tin oxide glass substrates (24×25 mm$^2$). The coated substrates were dried at 80° C. for 30 min and then illuminated with linearly polarised ultra-violet light at 300.5 nm from an argon ion laser using the set-up shown in FIG. 4. The film anisotropy against UV exposure time was measured by determining the induced birefringence using a He-Ne laser at 632.8 nm. By the method described Twisted and non-twisted nematic cells were prepared by combining the photoaligned substrate with a unidirectionally rubbed polyimide substrate whose orientation direction was either parallel or orthogonal to that of the photoaligned substrate. An uniform cell gap was obtained by using mylar spacers (17 μm). The cells were filled with a nematic mixture (Merck E202) at 89° C. under vacuum by capillary action. On cooling either a twisted nematic or a non-twisted cell was observed depending on how the substrates were combined. A twist angle of 90° was found for a twisted nematic cell using this cross-linked material exposed for 8 min at 2 mWcm$^{-2}$.

What is claimed is:

1. A compound of Formula I:

Formula I wherein
$X_{1-8}$ are each independently selected from: H, halogen, CN, OH, straight or branched chain alkyl having from 1 to 16 carbon atoms, where one or more non-adjacent $CH_2$ groups may be substituted by CH(CN), CH(CF$_3$), CHF, CHCl, CH(CH$_3$);
$S_{1-8}$ are spacer units;
$PG_{1-4}$ are photopolymerisable/dimerisable groups;
$m_1$, $m_2$, $m_3$, and $m_4$ are each independently selected from the integers 1 and 0;
$A_{1-8}$ are each independently selected from the aromatic rings:

where ~ indicates a sigma bond between part of the molecule shown in formula I and a carbon atom at any position in one of the aromatic rings;

and where the CH groups present in the aromatic rings may each be independently substituted by C(CN), C(CF$_3$), C-halogen, C(CH$_3$), CR, where R is selected from straight or branched chain alkyl and may include from 1 to 8 carbon atoms and including where one or more non-adjacent $CH_2$ groups may be substituted by CH(CN), CH(CF$_3$), CHF, CHCl, CH(CH$_3$).

2. A compound according to claim 1 wherein $S_{1-4}$ are, independently of one another, selected from groups having the general formula:

$$L_1-(CH_2)_n-L_2$$

where: n=1 to 30, where each $CH_2$ group present in the chain linking $L_1$ and $L_2$ may be independently substituted by CH(CN), CH(CF$_3$), CHF, CHCl, CH(CH$_3$), $L_1$ and $L_2$ are independently selected from: single covalent bond, O, COO, OOC, $CH_2O$, and $OCH_2$; and $S_{5-8}$ are each independently selected from: COO, OOC, C≡C, C=C, single covalent bond.

3. A compound according to claim 1 wherein $S_{1-4}$ are independently selected from oxycarbonylalkanoyloxy, oxyalkoxy, oxycarbonylalkoxy, oxyalkanoyloxy, oxycarbonylphenoxyalkanoyloxy, oxyalkoxyalkyl containing from 1–16 carbon atoms.

4. A compound according to claim 1 wherein $PG_{1-4}$ are, independently of one another, selected from:

where a sigma bond exists between part of the molecule shown in Formula I and any one of the four C atoms that are in the benzene ring to which G is fused and that do not form part of the ring G, and where CH groups present in the benzene ring, to which the ring G is fused, may each be independently substituted by C(CN), C(CF$_3$), C-halogen, C(CH$_3$), CR, where R is selected from straight or branched chain alkyl and may include from 1 to 8 carbon atoms and including where one or more non-adjacent $CH_2$ groups may be substituted by CH(CN), CH(CF$_3$), CHF, CHCl, CH(CH$_3$);

$R_1$ may be H, halogen, CN, NO$_2$, NCS, SCN, alkyl with 1 to 12 carbon atoms which is optionally substituted with one or more fluorines and in which optionally 1 or 2 non-adjacent methylene units (CH$_2$) can be replaced by oxygen, COO, OOC, CO and/or CH=CH;

D, may be H, alkyl or alkoxy with 1 to 8 carbon atoms, trifluoromethyl, or phenyl which may be substituted from one and up to and including all available substitution positions with one or more of the groups selected from CN, halogen, NO$_2$;

$E_1$ may be H, alkyl or alkoxy with 1 to 8 carbon atoms, cyano, or COOR$_5$;

$R_5$ may be $C_{1-10}$ alkyl;

where G is independently selected from:

$R_2$ may be H or $C_{1-10}$ alkyl;

$D_2$ may be H, alkyl or alkoxy with 1 to 8 carbon atoms, trifluoromethyl, or phenyl which may be substituted from one and up to and including all available substitution positions with one or more of the groups selected from CN, halogen, $NO_2$: $E_2$ may be H, alkyl or alkoxy with 1 to 8 carbon atoms, cyano, or $COOR_6$;

$R_6$ may be $C_{1-10}$ alkyl;

$D_3$ may be H, alkyl or alkoxy with 1 to 8 carbon atoms, trifluoromethyl, or phenyl which may be substituted from one and up to and including all available substitution positions with one or more of the groups selected from CN, halogen, $NO_2$;

$E_3$ may be H, alkyl or alkoxy with 1 to 8 carbon atoms, cyano, or $COOR_7$;

$R_7$ may be $C_{1-10}$ alkyl.

$D_4$ may be H, alkyl or alkoxy with 1 to 8 carbon atoms, trifluoromethyl, or phenyl which may be substituted from one and up to and including all available substitution positions with one or more of the groups selected from CN, halogen, $NO_2$;

$E_4$ may be H, alkyl or alkoxy with 1 to 8 carbon atoms, cyano, or $COOR_8$;

$R_8$ may be $C_{1-10}$ alkyl.

and where J is independently selected from:

$D_5$ may be H, alkyl or alkoxy with 1 to 8 carbon atoms, trifluoromethyl, or phenyl which may be substituted from one and up to and including all available substitution positions with one or more of the groups selected from CN, halogen, $NO_2$;

$E_5$ may be H, alkyl or alkoxy with 1 to 8 carbon atoms, cyano, or $COOR_9$;

$R_9$ may be $C_{1-10}$ alkyl;

$D_6$ may be H, alkyl or alkoxy with 1 to 8 carbon atoms, trifluoromethyl, or phenyl which may be substituted from one and up to and including all available substitution positions with one or more of the groups selected from CN, halogen, $NO_2$;

$E_6$ may be H, alkyl or alkoxy with 1 to 8 carbon atoms, cyano, or $COOR_{10}$, $R_{10}$ may be $C_{1-10}$ alkyl.

5. A method of providing an alignment layer on a surface of a liquid crystal cell wall comprising the steps of depositing a layer of material comprising at least one compound according to any of claims 1–4 on the surface;

exposing the material to actinic radiation.

6. A method according to claim 5 characterised in that the method further comprises the step of controlling the exposure time and/or intensity of the actinic radiation used to provide a selected value of pretilt in a liquid crystal placed in contact with the exposed layer.

7. A liquid crystal device comprising a layer of liquid crystal material between two cell walls, the cell walls at least one carrying electrode structures and surface treated to provide an alignment layer for liquid crystal molecules;

characterised in that the alignment layer comprises a compound according to any of claims 1–4 which has been exposed to actinic radiation.

8. A liquid crystal device according to claim 7 characterised in the alignment layer comprises a compound according to claims 1–4 that has been exposed to actinic radiation, the exposure time and/or intensity of the actinic radiation used being controlled to provide a selected value of pretilt in a liquid crystal placed in contact with the exposed layer.

9. A liquid crystal device according to claim 6 wherein the device is an Active Matrix Device.

10. A liquid crystal device according to either of claims 6 and 7 wherein the device is an STN device.

11. A method according to claim 5 wherein the radiation is in the range 250–450 nm.

12. A device according to claim 6 wherein the radiation is in the range 250–450 nm.

* * * * *